(12) United States Patent
Drew

(10) Patent No.: US 12,220,553 B2
(45) Date of Patent: Feb. 11, 2025

(54) IMPLANTABLE ACCESS PORT WITH ONE-DIRECTIONAL FILTER

(71) Applicant: Medtronic, Inc., Minneapolis, MN (US)

(72) Inventor: Touby A. Drew, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/223,639

(22) Filed: Jul. 19, 2023

(65) Prior Publication Data

US 2023/0364405 A1    Nov. 16, 2023

Related U.S. Application Data

(62) Division of application No. 17/085,569, filed on Oct. 30, 2020, now Pat. No. 11,745,003.

(51) Int. Cl.
*A61M 39/02* (2006.01)
*A61M 39/04* (2006.01)

(52) U.S. Cl.
CPC ........ *A61M 39/0247* (2013.01); *A61M 39/04* (2013.01); *A61M 2039/0241* (2013.01);
(Continued)

(58) Field of Classification Search
CPC .............. A61M 39/0247; A61M 39/04; A61M 2039/0241; A61M 2039/027;
(Continued)

(56) References Cited

U.S. PATENT DOCUMENTS

| 5,045,064 A | 9/1991 | Idriss |
| 5,085,644 A | 2/1992 | Watson et al. |

(Continued)

FOREIGN PATENT DOCUMENTS

| CN | 208838708 U | 5/2019 |
| WO | WO 2000/066204 A1 | 11/2000 |

(Continued)

OTHER PUBLICATIONS

Alcyone Lifesciences, Inc., Bringing Hope to Spinal Muscular Atrophy (SMA) Patients with the Alcyone Lifesciences ThecaFlex DRx™ System Breakthrough Device, Dec. 2, 2019, 3 pages, available at: https://www.prnewswire.com/news-releases/bringing-hope-to-spinal-muscular-atrophy-sma-patients-with-the-alcyone-lifesciences-thecaflex-drx-system-breakthrough-device-300967222.html.

*Primary Examiner* — Theodore J Stigell
(74) *Attorney, Agent, or Firm* — Husch Blackwell LLP

(57) ABSTRACT

An implantable access port including a port housing that defines a fill port cavity and includes a catheter fitting, a filter positioned within the port housing along a delivery flow pathway configured so that fluid injected into the fill port cavity passes through the filter prior to exiting through the catheter fitting, a one-way valve positioned within the port housing along an aspiration flow pathway configured to permit aspirated fluid to flow unfiltered from the catheter fitting to the fill port cavity and prevent injected fluid from flowing unfiltered from the fill port cavity to the catheter fitting, a port cover coupled to the port housing, and a pierceable septum positioned between the fill port cavity and the port cover configured to allow a needle to pierce through the pierceable septum to access the fill port cavity.

9 Claims, 9 Drawing Sheets

(52) U.S. Cl.
CPC .............. *A61M 2039/027* (2013.01); *A61M 2039/0273* (2013.01); *A61M 2039/0276* (2013.01); *A61M 2210/1003* (2013.01)

(58) Field of Classification Search
CPC .. A61M 2039/0273; A61M 2039/0276; A61M 2210/1003; A61M 2039/0217; A61M 2205/75; A61M 39/0208; A61M 2039/0202; A61M 2039/0205; A61M 2039/0223; A61M 39/02
See application file for complete search history.

(56) References Cited

U.S. PATENT DOCUMENTS

| | | | |
|---|---|---|---|
| 5,281,210 | A | 1/1994 | Burke et al. |
| 5,527,307 | A | 6/1996 | Srisathapat et al. |
| 5,695,490 | A * | 12/1997 | Flaherty ............ A61M 39/0208 |
| | | | 604/288.02 |
| 5,702,372 | A | 12/1997 | Nelson |
| 5,833,654 | A | 11/1998 | Powers et al. |
| 5,957,890 | A | 9/1999 | Mann et al. |
| 6,013,051 | A * | 1/2000 | Nelson .............. A61M 39/0208 |
| | | | 604/93.01 |
| 6,042,579 | A | 3/2000 | Elsberry et al. |
| 6,572,583 | B1 | 6/2003 | Olsen et al. |
| 6,852,106 | B2 | 2/2005 | Watson et al. |
| 6,962,577 | B2 | 11/2005 | Tallarida et al. |
| 7,351,239 | B2 | 4/2008 | Gill |
| 7,366,562 | B2 | 4/2008 | Dukesherer et al. |
| 7,637,897 | B2 | 12/2009 | Ginggen |
| 7,803,143 | B2 | 10/2010 | Tallarida et al. |
| 7,963,956 | B2 | 6/2011 | Kunst |
| 8,320,991 | B2 | 11/2012 | Jascob et al. |
| 8,419,710 | B2 | 4/2013 | Keimel et al. |
| 8,483,802 | B2 | 7/2013 | Kalpin et al. |
| 8,545,484 | B2 | 10/2013 | Haase et al. |
| 8,591,456 | B2 | 11/2013 | Steinbach |
| 8,613,724 | B2 | 12/2013 | Lanier, Jr. et al. |
| 8,721,605 | B2 | 5/2014 | Brandt et al. |
| 8,915,893 | B2 | 12/2014 | Steinbach |
| 8,932,271 | B2 | 1/2015 | Hamatake et al. |
| 9,079,004 | B2 | 7/2015 | Wiley et al. |
| 9,427,553 | B2 | 8/2016 | Nelson |
| 9,433,764 | B2 | 9/2016 | East et al. |
| 9,744,338 | B2 | 8/2017 | East et al. |
| 9,782,536 | B2 | 10/2017 | Skutnik et al. |
| 9,919,102 | B2 | 3/2018 | John |
| 9,981,117 | B2 | 5/2018 | Brandt et al. |
| 9,993,600 | B2 | 6/2018 | Lanier, Jr. et al. |
| 10,238,851 | B2 | 3/2019 | Butziger et al. |
| 10,376,635 | B2 | 8/2019 | Haase |
| 10,589,024 | B2 | 3/2020 | John |
| 10,596,362 | B2 | 3/2020 | Fielder et al. |
| 10,625,060 | B2 | 4/2020 | Børgesen |
| 11,745,003 | B2 | 9/2023 | Drew |
| 2005/0124980 | A1 | 6/2005 | Sanders |
| 2005/0137537 | A1 | 6/2005 | Watson et al. |
| 2005/0256461 | A1 | 11/2005 | DiFiore et al. |
| 2007/0112291 | A1 | 5/2007 | Børgesen |
| 2010/0004638 | A1 | 1/2010 | Gibson |
| 2010/0030196 | A1 | 2/2010 | Hildebrand et al. |
| 2016/0089521 | A1 | 3/2016 | Dragoon et al. |
| 2017/0014611 | A1 | 1/2017 | Butziger et al. |
| 2017/0325685 | A1 | 11/2017 | Shachar et al. |
| 2018/0117243 | A1 | 5/2018 | Maguire |
| 2019/0009014 | A1 | 1/2019 | Chen et al. |
| 2019/0184139 | A1 | 6/2019 | Nelson et al. |
| 2019/0269850 | A1 | 9/2019 | Shih et al. |
| 2019/0308000 | A1 | 10/2019 | Hanson |
| 2020/0061362 | A1 | 2/2020 | Singh et al. |
| 2022/0134077 | A1 | 5/2022 | Drew |

FOREIGN PATENT DOCUMENTS

| | | |
|---|---|---|
| WO | WO 2009/129474 A1 | 10/2009 |
| WO | WO 2012/138854 A1 | 10/2012 |
| WO | WO 2013/134486 A4 | 9/2013 |
| WO | WO 2016/059162 A1 | 4/2016 |
| WO | WO 2020/046791 A1 | 3/2020 |

* cited by examiner

300 — MACHINE A PORT HOUSING TO DEFINE A FILL PORT CAVITY, A DELIVERY FLOW PATHWAY, AND AN ASPIRATION FLOW PATHWAY

302 — POSITION A FILTER WITHIN THE PORT HOUSING ALONG THE DELIVERY FLOW PATHWAY

304 — POSITION A ONE-WAY VALVE WITHIN THE PORT HOUSING ALONG THE ASPIRATION FLOW PATHWAY

306 — POSITION A PIERCEABLE SEPTUM OVER THE FILL PORT CAVITY

308 — COUPLE A PORT COVER TO THE PORT HOUSING SO THAT THE PIERCEABLE SEPTUM IS COMPRESSED BETWEEN THE PORT COVER AND THE PORT HOUSING.

FIG. 9

IMPLANTABLE ACCESS PORT WITH ONE-DIRECTIONAL FILTER

RELATED APPLICATION

This application is a division of U.S. application Ser. No. 17/085,569 filed Oct. 30, 2020, which is hereby fully incorporated herein by reference.

FIELD

The present disclosure relates generally to implantable medical devices, and more particularly implantable drug delivery ports (also referred to as access ports) used to deliver pharmaceutical agents to target regions in the body.

BACKGROUND

A variety of medical devices are used for acute, chronic, or long-term delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. Drug access ports or other fluid delivery devices can be used for chronic delivery of pharmaceutical agents. Typically, such devices provide therapy by periodic injections aided by the port or other device to gain access to key positions within a patient's body such as the cerebrospinal fluid (CSF).

Implantable drug infusion ports can provide important advantages over other forms of medicament administration. For example, oral administration is often difficult because the systematic dose of the substance needed to achieve the therapeutic dose at the target site may be too large for the patient to tolerate without adverse side effects. Also, some substances simply cannot be absorbed in the stomach adequately for a therapeutic dose to reach the target site. Moreover, substances that are not lipid soluble may not cross the blood-brain barrier adequately if needed in the brain via oral administration. Implantable access ports can help with these issues as well as help avoid the problem of patient noncompliance.

Implantable access ports are typically implanted at a location within the body of a patient (typically a subcutaneous region in the lower abdomen) and are configured to deliver a fluid medicament through a catheter to a target treatment site. Access ports typically receive percutaneous bolus injections via a syringe—the needle of the syringe is inserted through the skin of the patient, piercing a septum of the implantable access port. The pharmaceutical agent is injected into the implantable access port, which then delivers the pharmaceutical agent to the target treatment site via a catheter. The catheter used in these devices is generally configured as a flexible tube with a lumen running the length of the catheter that transports the pharmaceutical agent from the access port to a target treatment site within the patient's body.

Access ports may include antimicrobial filters having low mesh sizes on the order of about 0.2 microns. These filters allow for the removal of select particulates, agglomerates, microbials, and the like, if present, from the injected therapeutic fluid. However, due to the mesh size of such filters, they can prevent the ability for aspiration of a sample fluid from the target treatments site (e.g., cerebral spinal fluid (CSF)) where the filter may prevent biological markers, proteins, or other large constituents and the like from being collected.

One approach to the above problem may be to use two catheters coupled to the delivery device with dedicated flow paths within the device for delivery and sample. This approach however can require a larger delivery device and more invasive catheter tunneling within the patient as well as dedicated entry sites within the port for gaining access to the different pathways. An alternative approach is to include port cavities and multiple septums within the device to allow for selection by the clinician for delivery or sampling of fluid. This approach likewise requires a larger delivery device with separate entry points on the device. Yet another approach is to exclude the presence of a filter altogether, which may be undesirable for certain types of medication or drug delivery locations.

The present disclosure may address one or more of these concerns.

SUMMARY

Embodiments of the present disclosure provide a drug delivery system including an access port in which the system includes a filtered delivery pathway and unfiltered aspiration pathway that may be selected by the clinician. The system is configured to allow delivery of a therapeutic fluid through the access port (e.g., via a bolus injection), that passes through a filter prior to being delivered to the target treatment site (e.g., CSF). Additionally, when aspirating fluid from the access port during fluid sampling, the sampled fluid bypasses the filter such that the aspirated fluid is collected unfiltered from the target treatment site. The term "unfiltered" as used herein means a fluid that does not pass through a biological retentive filter or does not pass thorough a filter media having a pore size less than about 1 µm, less than about 0.5 µm, or less than about 0.3 µm.

In an embodiment, the disclosure describes a system including an implantable access port including a port housing that defines a fill port cavity and includes a catheter fitting, a filter positioned within the port housing along a delivery flow pathway defined by the port housing, where the access port is configured so that fluid injected into the fill port cavity passes through the filter prior to exiting through the catheter fitting, a one-way valve positioned within the port housing along an aspiration flow pathway defined by the port housing, where the one-way valve is configured to permit aspirated fluid to flow unfiltered from the catheter fitting to the fill port cavity and prevent injected fluid from flowing unfiltered from the fill port cavity to the catheter fitting, a port cover coupled to the port housing, and a pierceable septum positioned between the fill port cavity and the port cover, where the cover defines an aperture positioned over the pierceable septum. The access port is configured to allow a needle to pierce through the pierceable septum to access the fill port cavity.

In another embodiment, the disclosure describes a method of forming an implantable access port including machining a port housing to define a fill port cavity, delivery flow pathway, and an aspiration flow pathway, where the port housing includes a catheter fitting configured to couple to a catheter. The method includes positioning a filter within the port housing along the delivery flow pathway defined by the port housing, where the access port is configured so that fluid injected into the fill port cavity passes through the filter prior to exiting through the catheter fitting, positioning a one-way valve within the port housing along the aspiration flow pathway defined by the port housing, where the one-way valve is configured to permit aspirated fluid to flow unfiltered from the catheter fitting to the fill port cavity and prevent injected fluid from flowing unfiltered from the fill port cavity to the catheter fitting, positioning a pierceable septum over the fill port cavity; and coupling a port cover to the port housing so the pierceable septum is positioned between the fill port cavity and the port cover, where the port cover defines an aperture positioned over the pierceable septum, wherein the drug delivery port is configured to allow a needle to pierce through the pierceable septum to access the fill port cavity.

In another embodiment, the disclosure describes an implantable access port including a port housing having a catheter fitting configured to couple to a catheter, where the port housing defines a fill port cavity. The access port further includes a port cover coupled to the port housing; a first pierceable septum positioned between the fill port cavity and the port cover, where the port cover defines an aperture positioned over the first pierceable septum, where the first pierceable septum is configured to be pieced by an external needle to grant the needle access to the fill port cavity, a second pierceable septum positioned within and dividing the fill port cavity into a delivery cavity and an aspiration cavity; and a filter positioned within the port housing along a delivery flow pathway defined by the port housing, where the access port is configured so that fluid injected into delivery cavity passes through the filter prior as it flows from the delivery cavity to the catheter fitting, and where the port housing defines an aspiration pathway configured to permit aspirated fluid to flow unfiltered from the catheter fitting to the aspiration cavity.

In another embodiment, the disclosure describes an implantable modular filter attachment including a proximal end configured to couple to a catheter fitting on an implantable drug delivery pump or access port; a distil end including a catheter fitting configured to couple to a catheter, a filter positioned along a delivery flow pathway defined by the implantable modular filter, where the implantable modular filter is configured so that fluid flowing from the proximal end to the distal end passes through the filter; and a one-way valve positioned along an aspiration flow pathway defined by the implantable modular filter, wherein the one-way valve is configured to permit fluid to flow unfiltered from the distal end to the proximal end and configured to prevent fluid flowing unfiltered from the proximal end to the distal end.

The above summary is not intended to describe each illustrated embodiment or every implementation of the subject matter hereof. The figures and the detailed description that follow more particularly exemplify various embodiments.

BRIEF DESCRIPTION OF DRAWINGS

FIG. 9 is a block diagram of an example method to form a disclosed access port.

Figure 1:
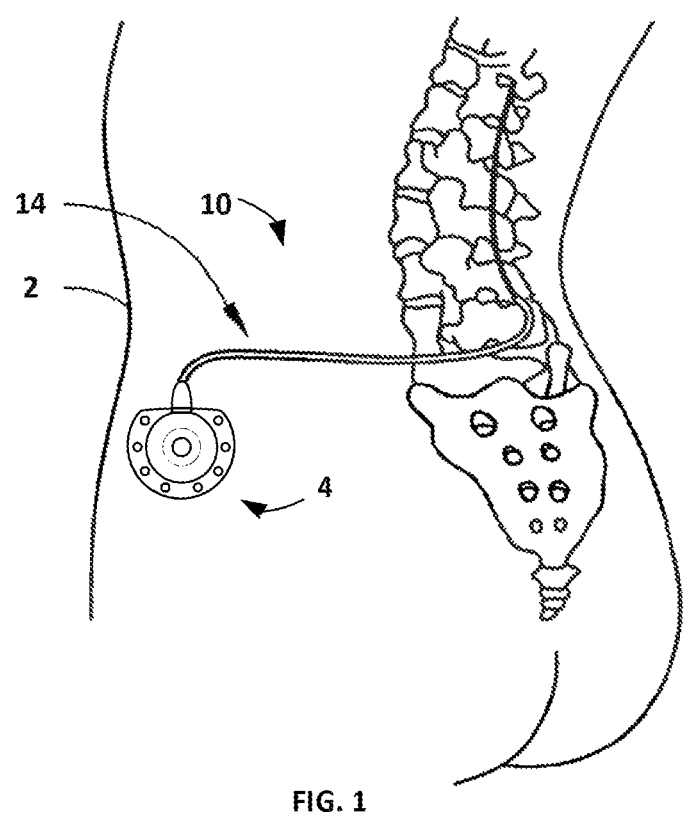
FIG. 1 is a schematic diagram of a portion of an implantable drug delivery system that includes an access port implanted within the body of a patient.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 is a schematic diagram showing an implanted drug delivery system 10 for introducing a therapeutic fluid to a target treatment site within the body of a patient 2. FIG. 1 shows the lower abdomen of patient 2 and drug delivery system 10, which includes access port 4 and catheter 14 implanted in patient 2. Although depicted in connection with a human body, it should be understood that drug delivery system 10 of the present invention could also be used on non-human animals.

Access port 4 may be used for infusing a fluid containing one or more pharmaceutical agents (e.g., a therapeutic fluid) into the various target locations of patient 2 such as the CSF within the spinal canal, deep brain structures, abdomen, or other desired treatment locations. Access ports mounted within the abdomen of a patient may be advantageous to deliver pharmaceutical agents directly to CSF within the spinal canal of a patient. This approach offers a less invasive alternative that relies on the indirect delivery of the pharmaceutical agent to the brain by delivering the agent to the CSF and relying on diffusion of the pharmaceutical agent within the CSF to reach the brain.

Access port 4 is configured to be implanted within patient 2 and receive a therapeutic fluid containing one or more pharmaceutical agents via a percutaneous bolus injection. The therapeutic fluid is then transported out of access port 4 and through catheter 14 to the target treatment site such as the CSF within patient 2. Access port 4 may be surgically implanted subcutaneously in the pectoral, abdominal, lower back region, or other desirable locations within patient 2.

Figure 2:
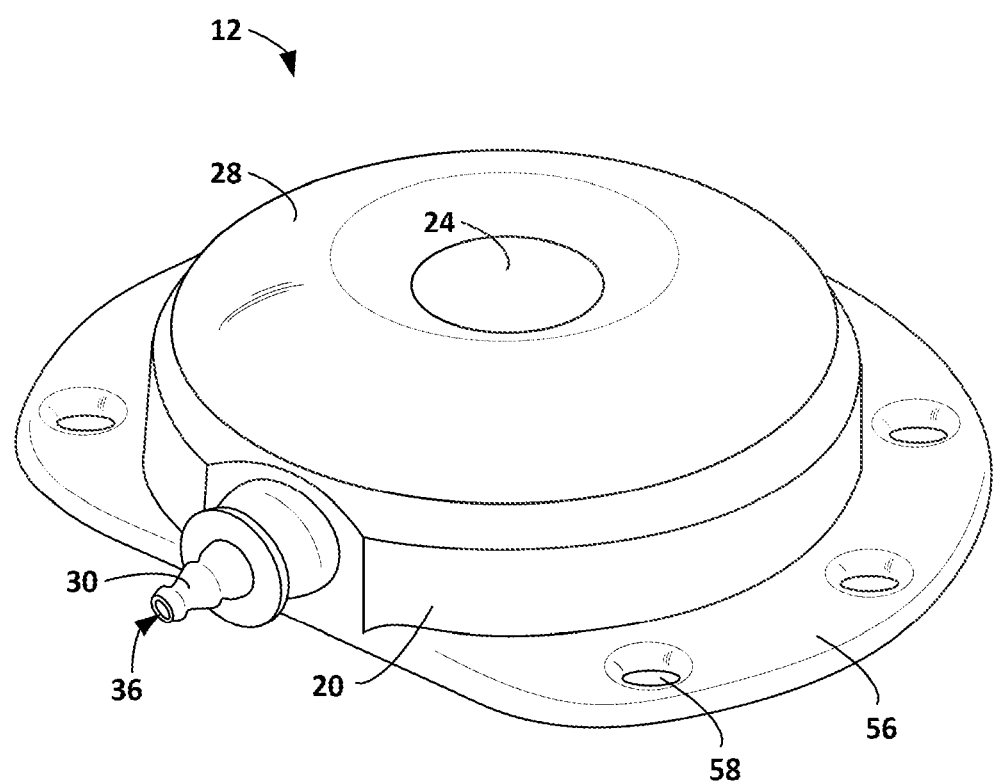
FIG. 2 is a schematic perspective view of an example access port that can be used with the drug delivery system of FIG. 1.
Figure 3:
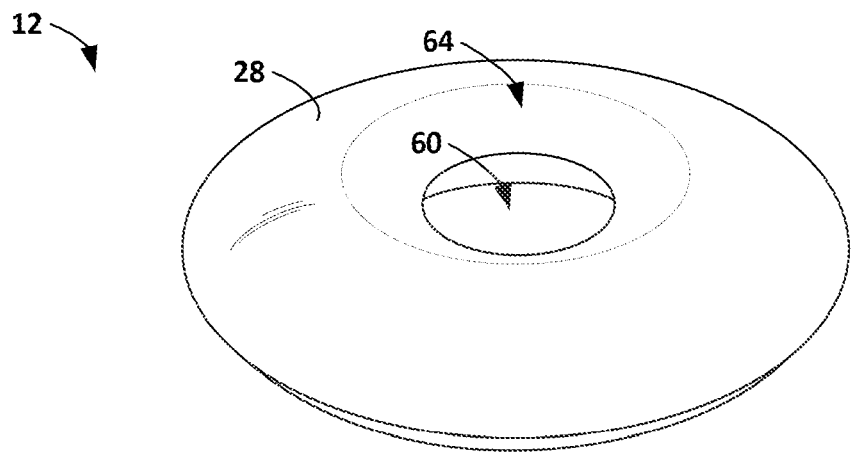
FIG. 3 is a schematic exploded view of the access port of FIG. 2.
Figure 3:
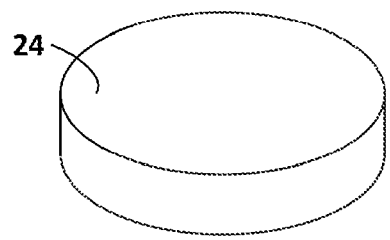
Figure 3:
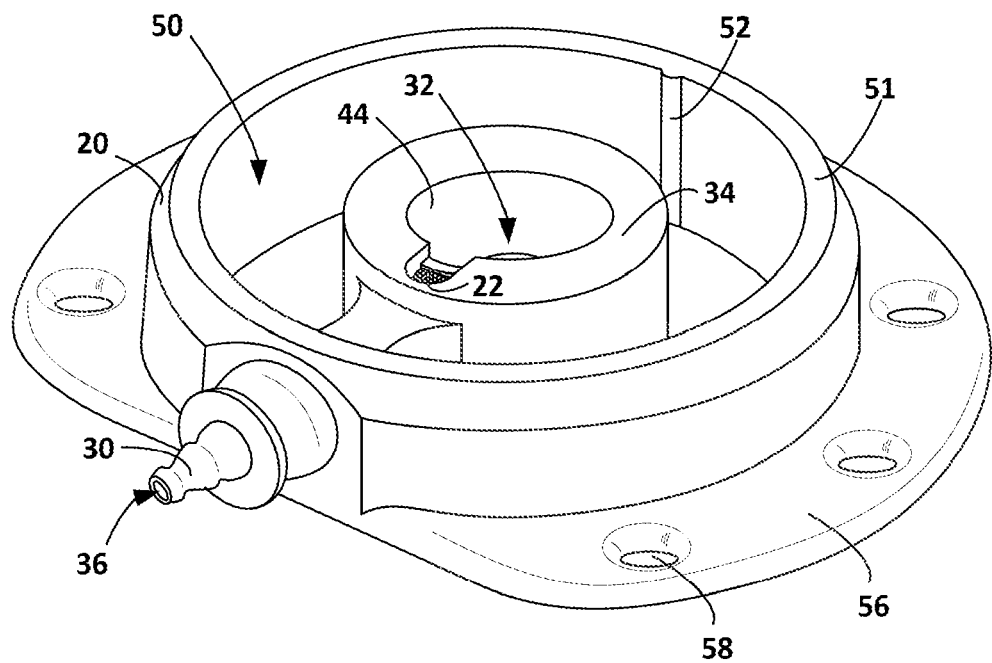
Figure 4:
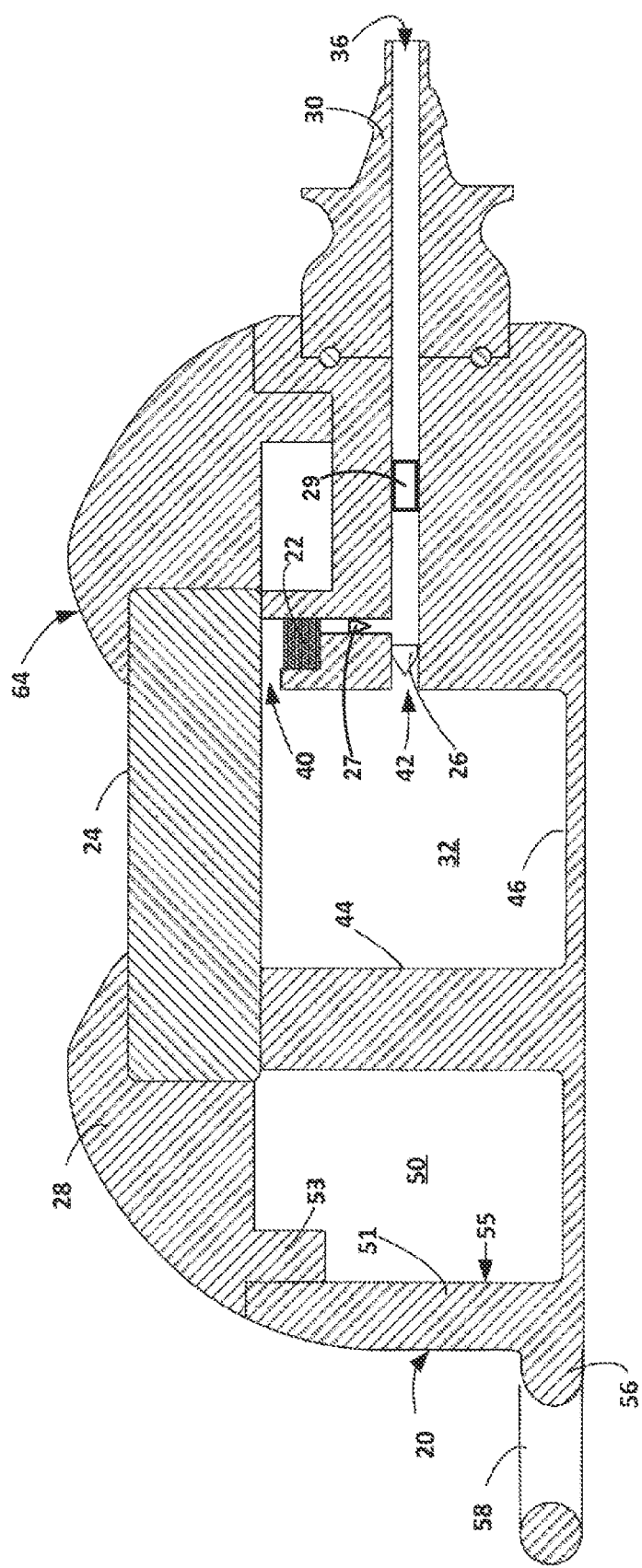
FIG. 4 is a schematic cross-sectional view of the access port of FIG. 2.

FIG. 2 is a schematic perspective view of an example access port 12 that can be used as access port 4 within drug delivery system 10 of FIG. 1. FIGS. 3 and 4 are schematic exploded and cross-sectional views respectively of access port 12 that illustrate various components of the port.

As shown in FIGS. 2-4, access port 12 includes a port housing 20, filter 22, septum 24, one-way valve 26, port cover 28, and catheter fitting 30. As discussed in further detail below, the interior of port housing 20 defines a fill port cavity 32 that is positioned near the center of port housing 20 and configured to receive a bolus injection of a therapeutic fluid. In an assembled state, septum 24 seats on an upper part of fill port cavity 32 such as a perimeter edge 34 such that an interior surface of septum 24 and fill port cavity 32 collectively form the reservoir volume of access port 12 that receives the injected therapeutic fluid.

Catheter 14 may be coupled to access port 12 via catheter fitting 30 which provides fluid communication with fill port cavity 32. To facilitate the connection, access port 12 may include multiple fluid pathways including a delivery pathway 40 and an aspiration pathway 42, both of which provide fluid communication (e.g., in parallel) between fill port cavity 32 and lumen 36 of catheter fitting 30.

Delivery pathway 40 represents the fluid pathway through access port 12 by which injected fluid into fill port cavity 32 will follow to be delivered to the target treatment site through catheter 14. Filter 22 may be positioned directly in line of delivery pathway 40 such that the injected fluid is forced to pass through filter 22 as the fluid travels to lumen 36 of catheter fitting 30. Upon exiting through lumen 36, the injected fluid passes through the lumen of catheter 14 where the fluid is introduced at the target treatment site (e.g., directly into the CSF within the spinal canal of patient 2).

Aspiration pathway 42 represents the fluid pathway through access port 12 by which collected fluid is withdrawn from the target treatment site (e.g., CSF) through lumen 36 via catheter 14 and into fill port cavity 32. One-way valve 26 may be positioned directly in line of aspiration pathway 42 to provide one-way flow between lumen 36 and fill port cavity 32. Fluid flowing through aspiration pathway 42 enters fill port cavity 32 unfiltered such that biological markers contained in the fluid are not removed and the fluid bypasses filter 22.

The directional flow through valve 26 may be based on a pressure differential across valve 26. For example, fluid flow may be initiated by the aspiration of fluid from fill port cavity 32. A sampling needle may be passed through septum 24 into fill port cavity 32 to withdraw fluid. The suction exerted on the sampled fluid via the needle may actuate valve 26 into an open-flow position allowing for fluid to easily flow from lumen 36 to fill port cavity 32 via aspiration pathway 42. With valve 26 in the open-flow position, the flow path through aspiration pathway 42 will be less restricted than the flow pathway through delivery pathway 40 and filter 22 thereby effectively bypassing fluid flow through delivery pathway 40 and promoting collection of fluid through aspiration pathway 42 during the aspiration procedure. Optionally if desired, delivery pathway 40 may also include a one-way flow valve 27 oriented in an opposite flow direction compared to valve 26 thereby preventing fluid from flowing through delivery pathway 40 during aspiration but permitting flow through the valve during fluid delivery.

During delivery of an injected fluid into fill port cavity 32, the injected fluid will create a head pressure across valve 26 thereby actuating the valve to a closed-flow position and stopping fluid flow through aspiration pathway 42 and promoting flow through delivery pathway 40 and filter 22.

Aspiration pathway 42 may be sufficiently sized so as to allow sampled fluid (e.g. CSF) to be collected in an unfiltered state. The flow pathway may be characterized by a minimum flow cross-section which defines the narrowest cross-sectional width (e.g., diameter) along a given pathway. In some examples, the minimum flow cross-section through aspiration pathway 42 may be greater than about 75 µm when valve 26 is in an open-flow position. In contrast, the minimum flow cross-section of delivery pathway 40 may be characterized by the mesh or pore size of filter 22 which may be on the order of about 0.2 µm.

Delivery and aspiration pathways 40 and 42 may be formed within port housing 20 using any suitable technique. In some examples, the different pathways may be produced by mechanical machining (e.g., CNC, or mechanical drilling), electrical discharge machining (EDM), combinations thereof, or the like.

Referring back to port housing 20, in some examples, fill port cavity 32 may be constructed as a cylindrical chamber that is defined by an inner sidewall 44 and needle stop 46 of port housing 20. Needle stop 46 forms a lower surface of fill port cavity 32 (e.g., the surface opposite of septum 24) and acts as a stop barrier for a needle introduced into fill port cavity 32 through septum 24. While needle stop 46 is generally shown as being a circular, flat surface, in other examples the surface of needle stop 46 may take on a different shape or design including, for example, domed or conical. The upper portion of sidewall 44 may terminate in perimeter edge 34 which is brought into direct contact against septum 24, however other possible arrangements are also envisioned.

In some embodiments, port housing 20 may also include a large-debris filter 29 disposed along delivery pathway 40, aspiration pathway 42, or both. The large-debris filter 29 may include a plurality of apertures or channels configured to prevent the flow of large particulate matter (e.g., core tear-outs from septum 24) through the various flow pathways. In contrast to filter 22, large-debris filter 29 is configured so that fluid passing through large-debris filter 29 remains "unfiltered" in that any biological markers within the fluid remain and are not removed by large-debris filter 29. Large-debris filter 29 may be considered as having a pore size substantially larger (e.g., more than 100 times larger) than the pore size of filter 22.

Filter 22 may include any suitable type of filter media for filtering a therapeutic fluid. In some embodiments, filter 22 may include, but is not limited to, a biological retention filter for removing bacteria, pathogens, viruses, or other organisms, a biological filer for biological materials such as proteins or antibodies, a chemical filter for removing chemicals, a particle filter for removing particulates, a filter for removing air or gasses, combinations thereof or the like. In some examples, filter 22 may include a woven, membrane, or film filter, a porous media filter such as a sintered metal or polymer or foam material, and the like. In general, a sterile or biological filter may be characterized by a pore diameter of about 0.45 µm or less, or about 0.22 µm or less. In some embodiments, filter 22 may be characterized as having a pore or mesh size of less than about 0.5 µm, or less than about 0.3 µm.

One-way valve 26 may include any suitable type of valve that allows for the one-directional fluid flow through aspiration pathway 42. In some embodiments, valve 26 may include, but is not limited to, a diaphragm valve, a duckbill valve, a flapper valve, a reed valve, a spring valve, or other type of valves. In preferred embodiments, valve 26 may be considered a passive valve that is automatically actuated based on the pressure differential or fluid flow across the valve. Valve 26 should also be selected to minimize a pressure differential in the flow path at the location of valve 26 while also maintaining a fluid seal during delivery of an injected fluid.

As shown in FIG. 2, catheter fitting 30 may be machined to include a fir-tree, barb, flare, lip or other suitable style connector assembly for receiving and coupling to a proximal end of catheter 14 during system implantation. The design of catheter fitting 30 may be configured allow permanent, semi-permanent, or removable connection with catheter 14. In either case, it is desirable for catheter 14 to remain coupled to access port 12 during the operable life-span of the implanted system 10.

In some embodiments, catheter fitting 30 can be a separated element compared to port housing 12 that is coupled to port housing 12 during assembly. In such embodiments, catheter fitting 30 may include a gasket or seal to couple to port housing 20. Alternatively, catheter fitting 30 may be integrally formed with port housing 20 from the sample block of material so that catheter fitting need not be coupled to port housing.

In some embodiments, access port 12 may optionally include one or more void chambers 50 within the interior space of port housing 20. Void chamber 50 represents empty space within the interior of access port 12 and is fluidically isolated from fill port cavity 32 when access port 12 is assembled, nor does void chamber 50 play a role with the drug delivery process. Instead, void chamber 50 acts as a negative space to increase the overall size and volume of access port 12 without contributing to the overall weight of port 12. In some embodiments, void chamber 50 may be in the form of a semi cylindrical or horseshoe shape chamber coaxially aligned with fill port cavity 32, although other shapes and designs are also envisioned.

Void chamber 50 may be defined in part by exterior sidewall 51 of port housing 20 which contacts and is secured to port cover 28 upon assembly. Either exterior sidewall 51 or port cover 28 may include one or more alignment features (e.g., raised lip 53) that contributes to the proper alignment and seating of port cover 28 to port housing 20. In some examples, an interior surface 55 of exterior sidewall 51 may include one or more press-fit retainers 52 (e.g., a small protrusion) configured to produce a friction fit with port cover 28 when the two components are press fit together. Interior surface 55 may include one or more retainers 52 at one or more locations—for example, pairs of retainers 52 distributed at multiple locations around interior surface 55. Additionally, or alternatively, lip 53 of port cover 28 may include similar retainer features.

The retainers 52 provide temporary securement between port housing 20 and port cover 28 during the manufacturing process until port housing 20 and port cover 28 can be welded together by creating a tight press-fit between port housing 20 and port cover 28. The inclusion of retainers 52 thus eliminates the need to tack weld the two components together prior to formation of the seam weld.

The overall shape of port housing 20 may be cylindrical with catheter fitting 30 protruding radially outward from one side. In some embodiments, port housing 20 may also include a suture flange or skirt 56 containing one or more suture points 58 therein. Suture flange 56 may extend radially outward from the base of port housing 20 (e.g., side opposite where port cover 28 attaches) and may partially encircle port housing 20 so as to not interfere with the securement of catheter 14 to catheter fitting 42. Suture flange 56 may be integrally formed with port housing 20.

Port housing 20 and port cover 28 may be composed of any suitable material including, for example, constructed of a material that is biocompatible such as titanium, tantalum, stainless steel, plastic, ceramic, or the like. In some embodiments, port housing 20 may be constructed from a single piece of titanium. Titanium offers the advantages of being inert to both the patient as well as most pharmaceutical agents and solutions.

Septum 24 forms a seal against aperture 60 of port cover 28. Upon full assembly of access port 12, septum 24 may be compressed between port cover 28 and perimeter edge 34 to provide a secure seal there between.

Further, port cover 28 may have a partial torus shape such that it forms a smooth, convex contour with exterior wall 51 of port housing 20 while also helping to provide a funneling surface 64 toward aperture 60 and septum 24. Funneling surface 64 may assist with allowing the clinician to palpitate the location of septum 24 as well as help direct the tip of a needle toward aperture 60.

The exterior surfaces of access port 12 intended to be placed in direct contact with the patient may be smooth and rounded so as not to include any abrupt corners that may cause irritation to the patient.

Drug delivery system 10 also includes catheter 14 having an elongated tubular portion that extends from the proximal end coupled to catheter fitting 30 to a distal end and defines an inner catheter lumen. Drug delivered from access port 12 or sampled from the target treatment site passes through the lumen of catheter 14. When implanted for delivering drugs to the spinal region, at least a portion of catheter 14 is located within intrathecally within the CSF of the patient such that as drug exits catheter 14 and enters directly into the CSF such that the pharmaceutical agent does not contact other tissues or bodily fluids before reaching the CSF of the patient.

The body of catheter 14 may be constructed using any suitable material, e.g., an elastomeric tube. When implanted in the spinal canal, catheter 14 may be floating free in the CSF and may contact the spinal cord of the patient. As a result, catheter 14 may preferably be soft and flexible to limit any chance of damaging the spinal cord. Examples of some suitable materials include, but are not limited to, silicone rubber (e.g., polydimethyl siloxane) or polyurethane, both of which can provide good mechanical properties and are very flexible. Suitable materials for catheter 14 are also preferably chemically inert such that they will not interact with drugs or body tissue or body fluids over a long time period.

The inside diameter of catheter 14 is preferably large enough to accommodate expected infusion rates with acceptable flow resistance for delivery of the pharmaceutical agent to a target treatment site as known by those in the art. As an example, catheter 14 may have an outside diameter of about 1.2 millimeters (mm) to about 2.0 mm and an inside diameter of about 0.4 mm to about 0.6 mm. In some embodiments, catheter 14 may be about 5 centimeters (cm) to about 100 cm long to reach from, e.g., access port 12 implanted in the patient's abdomen to the spine.

The disclosed drug delivery system 10 may be used to treat various neurological diseases; examples are chronic pain, chronic pain, tremors, Parkinson's disease, cancer, epilepsy, urinary or fecal incontinence, sexual dysfunction, obesity, spasticity, gastroparesis, or other disorders. Various types of pharmaceutical agents may be used for the treatment of such diseases. Examples of possible pharmaceutical agents that can be used with system 10 include, but is not limited to, one or more of Gabapentin, Baclofen, Midazolam, or Valproate Na for the treatment of epilepsy; insulin for the treatment of diabetes, analgesics for pain management; and the like. For effective delivery, the distal end of catheter 14 may be positioned within the CSF, portions of the brain, other parts of the body, or combinations thereof.

Figure 5:
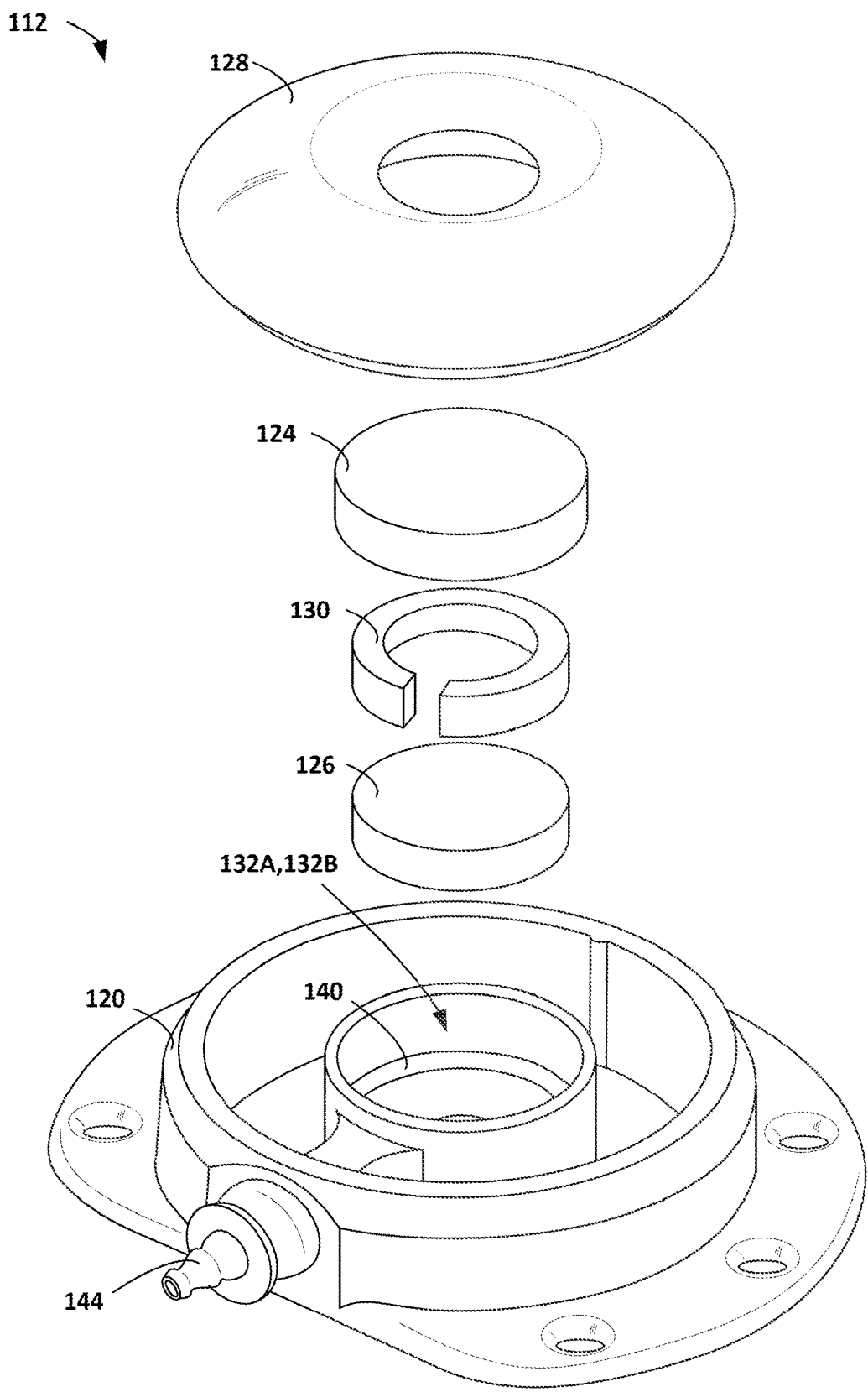
FIG. 5 is a schematic exploded view of another example access port that can be used with the drug delivery system of FIG. 1.
Figure 6:
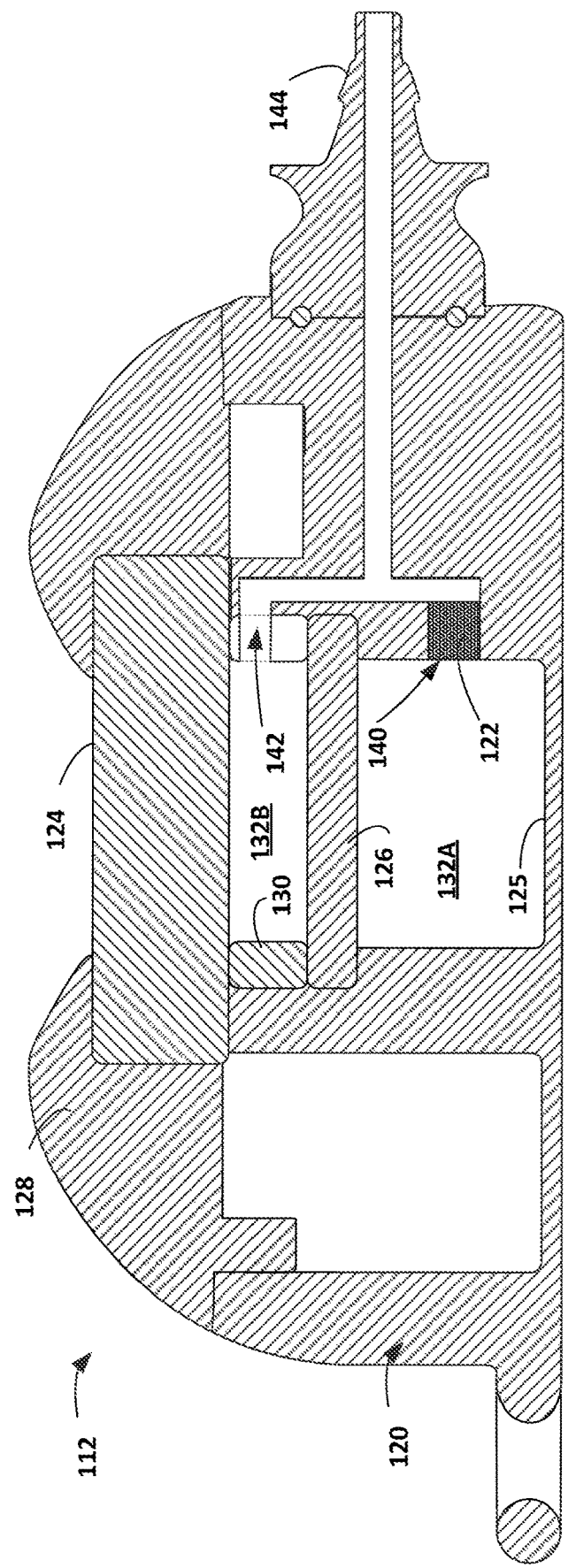
FIG. 6 is a schematic cross-sectional view of the access port of FIG. 5.

In other embodiments, access port 4 may include delivery and aspiration flow pathways that are selectable by the clinician via the use of a specialty needle. For example, FIG. 5 is a schematic exploded view of another example access port 112 that can be used as access port 14 in drug delivery system 10 of FIG. 1. FIG. 6 is a schematic cross-sectional view of access port 112. Access port 112 includes a port housing 120, filter 122, external septum 124, internal septum 126, port cover 128, and port cavity spacer 130. Port housing 120 defines a fill port cavity that is divided into a delivery cavity 132A and an aspiration cavity 132B separated by internal septum 126. In an assembled state, internal septum 126 seats along of a perimeter edge 140 of the chamber forming delivery cavity 132 to provide fluid separation between delivery and aspiration chambers 132A and 132B. Port cavity spacer 130 may be positioned between internal and external septums 126 and 124 to provide compression there between. In FIG. 5, spacer 130 is illustrated as a C-washer however other configurations and shapes are also envisioned.

The separation between delivery and aspiration cavities 132A and 132B created by internal septum 126 allow for the clinician to selectable access one cavity over another for the delivery or aspiration of fluid. For example, for delivery of a therapeutic fluid, the clinician may use a standard delivery needle to pierce both external and internal septums 124 and 126 to inject the fluid into delivery cavity 132A. The fluid will then follow along delivery pathway 140 where the fluid will pass through filter 122 prior to exiting through catheter fitting 144.

To perform aspiration, the clinician may select a specialty needle having a lumen opening positioned proximal to the piercing tip. Thus upon piecing access port 112, the needle tip may pass through both external and internal septums 124 and 126 hitting the needle stop 125, but providing only fluid access to aspiration cavity 132B via the needle lumen. Fluid aspiration may occur though aspiration pathway 142 pulling unfiltered fluid through catheter fitting 144 without having the fluid pass through filter 122. Alternatively, a clinician may use a standard hypodermic needle to access the aspiration cavity by relying on feel to ensure the needle does not pass through internal septum 126.

The construction of access port 112 allows for the aspiration of unfiltered fluid without the need to include a one-way valve in the port. Additionally, or alternatively, the construction of access port 112 also allows the clinician to deliver unfiltered therapeutic fluid directly to catheter 14 by using aspiration cavity 132B and aspiration pathway 142.

While the stacked orientation of delivery cavity 132A and aspiration cavity 132B may be in a configuration opposite of that shown in FIGS. 5 and 6 (e.g., delivery cavity 132A and filter 122 positioned between external and internal septums 124 and 126), having delivery cavity 132A and filter 122 positioned at the bottom of the stack and adjacent to needle stop 125 of port housing 120 may provide added safety benefits. For example, while access to aspiration cavity 132B may be granted with the use of a specialty needle, a conventional hypodermic needle where the lumen is positioned at the needle tip will access only delivery cavity 132A if fully introduced through septums 124 and 126. Thus, delivery pathway 140 through filter 122 may be considered the default pathway through access port 112 requiring conscious effort and needle selection on part of the clinician to access aspiration cavity 132B insuring injected fluid by default will be filtered prior to entry into the target treatment site.

Figure 7:
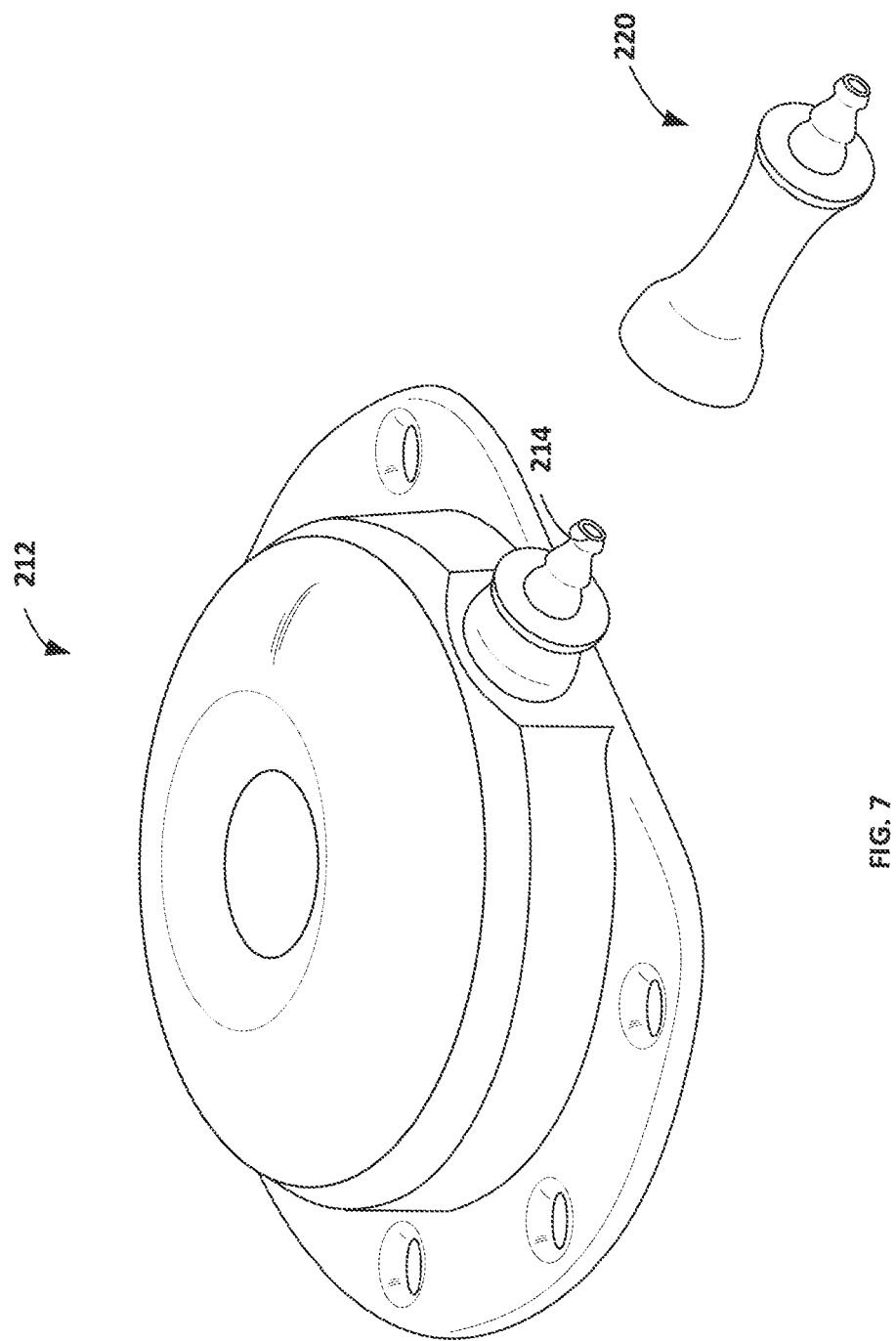
FIG. 7 is a schematic perspective view of another example access port and modular filter attachment that can be used with the drug delivery system of FIG. 1.
Figure 8:
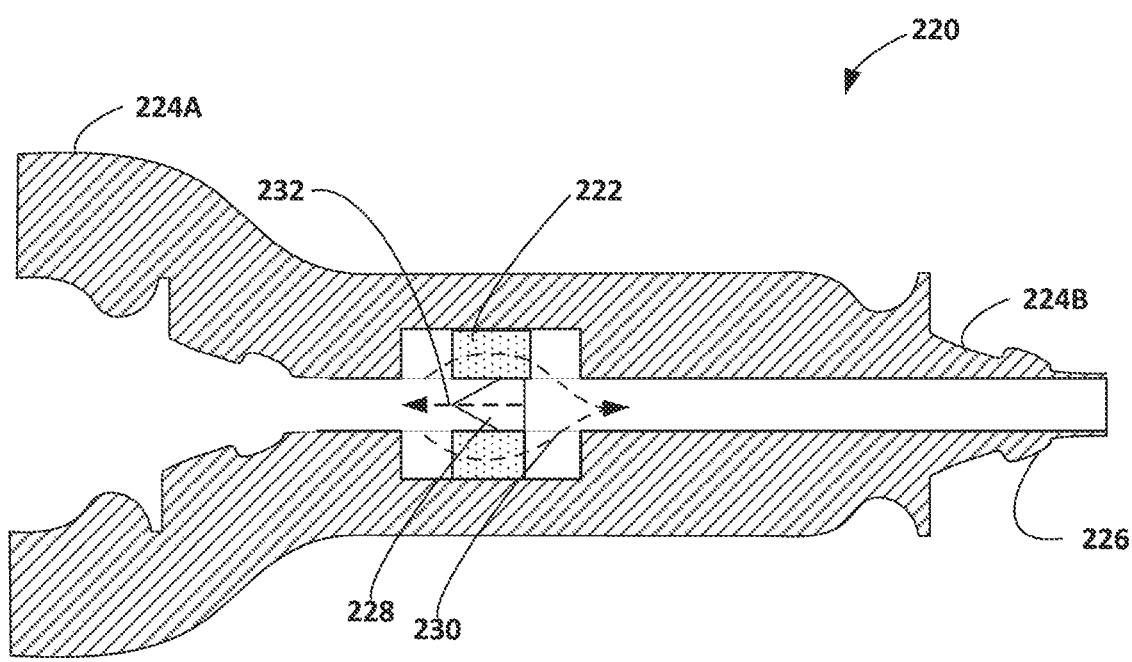
FIG. 8 is a schematic cross-sectional view of the modular filter attachment of FIG. 7.

In another embodiment, drug delivery system 10 may include a non-filtering access port that can be coupled with a modular filter attachment configured to filter injected fluid while also allowing for unfiltered aspiration to occur. FIG. 7 is a schematic perspective view of an example access port 212 and modular filter attachment 220 that can be used with the drug delivery system 10 of FIG. 1. FIG. 8 is a schematic cross-sectional view of modular filter 220 of FIG. 7.

Access port 212 may include any suitable access port having a catheter fitting 214 or fitting configured to couple with modular filter attachment 220. In some embodiments access port 212 may be a non-filtering device in the sense that fluid injected or aspirated from port 212 does not pass through a biological retentive filter or filter media that may reduce the presence of biological markers in a fluid.

Modular filter attachment 220 may couple to catheter fitting 214 of access port 212 during implantation to provide the clinician the opportunity to include or exclude the presence of a filter with port 212. Further, modular filter attachment 220 can allow the clinician to select the filter 222 included with system 10, thereby allowing for customization of the drug delivery device and tailorability of the system to a particular pharmaceutical fluid or treatment procedure.

Modular filter attachment 220 includes a proximal end 224A configured to couple with catheter fitting 214 and a distal end 224B having a catheter fitting 226 configured to couple with a catheter 14. Modular filter attachment 220 includes a filter 222 and a one-way valve 228 configured so that delivery of a therapeutic fluid passing from proximal end 224A to distal end 224B of modular filter attachment 220 is passed through filter 226 along delivery pathway 230. The action of one-way valve 228 prevents the flow of fluid in the proximal-to-distal direction thereby forcing all fluid being delivered to pass through filter 222.

In contrast, during aspiration fluid is withdrawn into access port 212 thereby forcing the reverse flow of fluid through modular filter attachment 220 from distal end 224B to proximal end 224A along aspiration pathway 232. The distal-to-proximal direction of fluid flow causes one-way valve 232 to open and permit the flow of fluid through modular filter attachment 220 without needing to pass through filter 222, thereby allowing for the collection of unfiltered sample fluid.

FIG. 9 is a flow diagram illustrating an example method of forming access port 4 of drug delivery system 10. The method of FIG. 9 is primarily used to describe the formation of access ports 12 however the method may be used to form other access ports or access port 12 may be form using other methods.

FIG. 9 machining a port housing 20 of access port 12 to define fill port cavity 32, delivery flow pathway 40, and an aspiration flow pathway 42 (300), positioning a filter 22 within port housing 20 along delivery flow pathway 40 (302), positioning one-way valve 26 within port housing 20 along aspiration flow pathway 42 (304), positioning pierceable septum 24 over fill port cavity 32 (306), and coupling port cover 28 to port housing 20 so pierceable septum 24 is positioned between fill port cavity 32 and port cover 28. As discussed above, delivery and aspiration pathways 40 and 42 may be configured so that fluid injected into fill port cavity 32 passes through filter 22 along delivery pathway 40 and is prevented from flowing through aspiration pathway 42 by one-way valve 26. Additionally, delivery and aspiration pathways 40 and 42 may be configured so that fluid and fluid aspirated from fill port cavity 32 via a needle passes through one-way valve 26 along aspiration pathway 42 unfiltered without passing through filter 22.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An implantable access port comprising:
   a housing comprising a catheter fitting configured to couple to a catheter;
   a fluid reservoir disposed within the housing, the fluid reservoir comprising a sidewall and a needle stop;
   a port cover coupled to the housing;
   a first pierceable septum positioned between the fluid reservoir and the port cover, wherein the port cover defines an aperture positioned over the first pierceable septum, and wherein the first pierceable septum is configured to be pierced by an external needle to grant the needle access to the fluid reservoir;
   a second pierceable septum positioned within the fluid reservoir to define a delivery cavity and an aspiration cavity within the fluid reservoir, wherein the aspiration cavity is positioned between the first pierceable septum and the second pierceable septum and the delivery cavity is positioned between the second pierceable septum and the needle stop; and
   a filter positioned within a delivery pathway defined by the housing, wherein the access port is configured so that a delivered fluid injected into the delivery cavity passes through the filter as the delivered fluid flows from the delivery cavity to the catheter fitting, and wherein the housing further defines an aspiration pathway configured to permit an aspirated fluid to flow unfiltered from the catheter fitting to the aspiration cavity.

2. The implantable access port of claim 1, wherein the filter comprises a biological retentive filter.

3. The implantable access port of claim 1, wherein the filter comprises a chemical filter.

4. The implantable access port of claim 1, wherein the filter comprises a particle filter.

5. The implantable access port of claim 1, wherein the filter defines a pore size of less than about 0.45 micrometers ($\mu m$).

6. The implantable access port of claim 1, wherein all delivered fluid injected into the delivery cavity passes through the filter.

7. The implantable access port of claim 1, further comprising a large-debris filter configured to prevent needle tear-outs of the first pierceable septum from entering the delivery fluid pathway upon injection of the delivered fluid into the delivery cavity.

8. The implantable access port of claim 1, wherein the aspiration pathway comprises a minimum cross-sectional width of greater than about 75 $\mu m$.

9. The implantable access port of claim 1, wherein the access port comprises no fluid pathways between the fluid reservoir and the catheter fitting other than the aspiration pathway and the delivery pathway.

* * * * *